United States Patent [19]

Grangeat

[11] Patent Number: 5,124,914
[45] Date of Patent: Jun. 23, 1992

[54] METHOD AND DEVICE FOR OBTAINING TRIDIMENSIONAL OPTICAL IMAGE FORMATION FROM BIDIMENSIONAL MEASUREMENTS OF ATTENUATION OF RADIATION THROUGH AN OBJECT

[75] Inventor: Pierre Grangeat, Echirolles, France

[73] Assignee: Commissariat a l'Energie Atomique, Paris, France

[21] Appl. No.: 310,726

[22] PCT Filed: May 20, 1988

[86] PCT No.: PCT/FR88/00254
§ 371 Date: Jan. 9, 1989
§ 102(e) Date: Jan. 9, 1989

[87] PCT Pub. No.: WO88/09148
PCT Pub. Date: Dec. 1, 1988

[30] Foreign Application Priority Data

May 21, 1987 [FR] France ................. 87 07134

[51] Int. Cl.⁵ .............................. G06F 15/42
[52] U.S. Cl. ................. 364/413.16; 364/413.19
[58] Field of Search ............... 364/413.13, 413.19, 364/413.16, 413.01

[56] References Cited

U.S. PATENT DOCUMENTS 4,520,442 5/1985 Grimberg et al. ............. 364/413.13
4,578,752 3/1986 Klansz ........................... 364/413.19
4,578,753 3/1986 Crawford et al. ............. 364/413.19

OTHER PUBLICATIONS

Kowalski, G., "Multislice Reconstruction From Twin-Cone Beam Scanning", IEE Tran on Nac. Sci. vol. NS-26, No. 2, Apr. 1979 pp. 2895-2903.
Schlindwein, M., "Interactive Three Dim. Recon. From Twin Beam Proj.", IEE Trans. on Nuc. Sci., vol. NS-25 No. 5, Oct. 1978 pp. 1135-1143.
Minesho, G. N., "Convolational Recon. From CME-Beam Proj. Data", IEEE Transactions on Nuclear Sci., vol. NS-26, No. 2, Apr. 1979, pp. 2682-2684.
Nahamoo, D. et al., "Design Constraints and Reconstruction Algorithms for Transverse-Cont-Rotate CT Scanner", IEEE Tran on Nucl. Sci., vol. BME-28, No. 2 1981, pp. 79-98.
Physics in Medicine and Biology, Moore S. C. et al., "Inversion of the 3D Transform for Multidetector point-focused SPECT brain Scanner", pp. 207-221.

Primary Examiner—Gail O. Hayes
Attorney, Agent, or Firm—Oblon, Spivak, McClelland, Maier & Neustadt

[57] ABSTRACT

The use of the derivative of the Radon transform is used for obtaining three dimensional images or reconstructions of the examined objects. The derivative provides a precise reconstruction of the image as opposed to the use of Radon transforms themselves. The device is particularly suited for three dimensional imaging and x-ray apparatus.

20 Claims, 7 Drawing Sheets

METHOD AND DEVICE FOR OBTAINING TRIDIMENSIONAL OPTICAL IMAGE FORMATION FROM BIDIMENSIONAL MEASUREMENTS OF ATTENUATION OF RADIATION THROUGH AN OBJECT

BACKGROUND OF THE INVENTION

1. Field of the Invention

The present invention relates to a method for obtaining tridimensional optical image formation of an object by means of irradiations, as well as a device used for the application of this method. A tridimensional reconstruction is effected by the processing of a series of bidimensional measurements of attentuation of radiation through the object, the incidence of radiation being modified between said measurements.

2. Description of the Prior Art

Bidimensional optical image formation from bidimensional measurements of the attenuation of radiation is well-known. The equipment comprises a source of suitable radiations, such as X-rays for medical examinations; the object to be examined is placed between the irradiating source and a sheet of paper or sensitive film whose points have an image produced according to the intensity of the rays at the outlet of the object; the contrasts observed concerning the image indicate the position of the absorbent zones of the object However, the information thus obtained is inadequate for certain applications and consequently methods for the tridimensional reconstruction of the object have been proposed.

Magnetic resonance tomography methods require the use of costly installations and extremely wide uniformity of the magnetic field where the object to be examined is placed. Moreover, the measuring times required to embody a tridimensional reconstruction are extremely long. Consequently, these drawbacks limit the advantages of these methods.

It has even been proposed to establish tridimensional reconstructions by the superimposition of bidimensional reconstructions or sections of the object. A collimation of an X-ray source makes it possible to obtain a fan-shaped radiation which traverses one section of the object and then produces an image of a line of sensors; the source rotates around the object so as to irradiate the same section under different angles; the successive measurements are stored and a computer makes it possible to determine local contribution on attenuation in each point of the meshing of the section. The source and the sensors are then offset and carried onto another section around which they move according to a trajectory parallel to the previous one.

The examination time thus depends on the adopted number of trajectories. In practice, it is unfortunately not possible to allow for an axial sampling as compacted as the sampling inside a section; the object also risks moving between examinations of the two sections, which increases localization uncertainties.

A further drawback is linked to collimation, which reduces the energy efficiency of the source and which may require that the device be stopped from time to time during the examination so as to allow it to cool down.

Methods have also been proposed which use a conical beam which rotates around the object and by which it is possible to carry out several irradiations which provide many bidirectional images of the object. If there is a sufficient number of these images, a computer can analyze and combine these images in order to reconstitute a tridimensional image of the object. These methods use what is known as the transformed Radon of the attenuation of radiation at each point of the meshing of the object. The transformed Radon of a function at a point is equal to all the sums of the local values of this function on each plane passing through at least one point of the range where the function is delivered. In practice, this clearly satisfies a discrete topology with a finite number of planes in order to describe the transformed Radon and a finite number of points in order to describe the function.

Measurement of attentuation of radiation on a line of sensors of a flat detector placed behind the object provides attenuation according to a beam of rays contained in a plane of the Radon space.

The sum of the attenuation along this line gives the value of the transformed Radon of attenuation for this plane. The numerical inversion of the transformed Radon gives attenuation at all points of the definition range of the function. It needs to be acknowledged that this entire process is complicated and that certain of the methods proposed result in erroneous results being obtained or all results nevertheless being inaccurate.

Amongst the literature available, reference may be made here to the article by Schlindwein and entitled "Iterative three—dimensional reconstruction from twin—cone beam projection" (IEEE Transactions on nuclear science, vol. NS-25, n°4, October 1978, pages 1135-1143), Where the methods using the transformed Radon are rejected owing to their complexity, and that of Minerbo entitled "Convolutional reconstruction from cone—beam projection data" (IEEE Transactions on nuclear science, vol. NS-26, n°2, April 1979, pages 2682-2684) which uses a method implementing the transformed Radon.

As revealed subsequently by the invention, the use of the transformed Radon itself nevertheless requires the use of approximations in the numerical calculations, and moreover the articles of the prior Art do not provide concrete devices allowing for reconstructions of good quality of tridimensional images.

SUMMARY OF THE INVENTION

The invention can overcome these drawbacks. First of all, it concerns tridimensional optical image formation devices, all of which comprise a single conical radiation source in front of the object and a detector bidimensional beam behind the object, the source and network being mobile along diverse incidences with respect to the object. It also concerns a method implementing the first derivative of the transformed Radon of attenuation of the radiation on the points of the object, its calculation and its inversion.

The samplings, required to obtain acceptable results, are mentioned. A detailed flowchart is proposed which in particular explains the interpolations.

A further object of the invention is to furnish trajectories of the source and the device for measurements to be made around the object and which are compatible with the method.

The invention first of all concerns a tridimensional optical image formation device by the irradiations of an object and comprising a radiation source irradiating a conical-shaped space in which the object is placed, a detector comprising a bidirectional device measuring attentuation of the radiation having traversed the object, a mechanism making it possible to carry out a series of irradiations of the object under different influences, as well as a measurement chain and a computer which analyses and processes the information of the bidimensional device during irradiations so as to deduce from this the local contribution at the different points of a meshing representing the object on attenuation of the radiation, wherein the source is unique and the computer comprises units suitable for carrying out the calculation and completing inversion of the derivative of the transformed Radon of a function being defined as all the local values of this function concerning each plane passing through at least one point of the range where the function is defined, and the derivative of the transformed Radon being defined as the sum of the variation rates concerning each of said planes if movement occurs perpendicular to said plane in the direction of the normal vector defined by a system of spherical coordinates.

According to one possible embodiment, the mechanism comprises a circular rail centered on an origin and on which the source carries out the irradiations according to a circular trajectory, the detector moving onto this same trajectory and occupying opposing positions with respect to the origin.

According to a more elaborate embodiment, the mechanism comprises two parallel circular rails, two sections on which slide respectively are the source and the detector both placed with opposing positions with respect to the origin. The sections pass through the circular trajectories when the irradiations are carried out. Moreover, these are bent back in the form of an arc of a circle in such a way that the source and detector remain at a constant distance from the origin.

The invention also concerns a method for the tridimensional optical image formation of an object from bidimensional measurements of the attenuation of a radiation through the object by the use of a device formed of a conical radiation source comprising a focal spot and a bidimensional detector formed of a network of sensors, wherein, in each of the first points of a meshing representing the object, attenuation is calculated of the radiation by calculating the variables representative of the derivative of the transformed Radon of attenuation of radiation of the points of a second meshing associated with the transformed Radon of the object, the transformed Radon of a function being defined as being all the local values of this function concerning each plane passing through at least one point of the range where the function is defined, and the derivative of the transformed Radon being defined as the sum of the variation rates concerning each of said planes if movement occurs perpendicular to said plane in the direction of the normal vector defined by a system of spherical coordinates, the quantities being calculated by adding up for each second point the variation of attenuation of radiation along at least one line obtained by intersection of the detector with a plane passing through the focal spot of the conical radiation and in the proximity of the second point, the straight line passing through the origin and the second point being roughly orthogonal to the plane passing through the focal spot, then linear combinations of these addings up, and the attenuation of radiation in each of the first points being obtained by derivation of these quantities with respect to the original distance, and finally by linear combination of the derived quantities, interpolations being effected moreover in order to pass from the second points to the first points.

The method may be advantageously used in the case where the source and the detector pass through two trajectories at a constant distance from the origin roughly in the form of a sinusoid comprising at least two periods out of a complete revolution around the object and whose amplitude is equal to or greater than the distance between the origin and any point of the object, the distance between the points of the trajectories and the origin being moreover sufficient so that any plane passing through the object will encounter the trajectory. For two periods, this is verified if this distance is equal to or greater than this amplitude multiplied by $\sqrt{3}$.

The method for reconstructing images according to the invention involves a special calculation method. For the calculation of a parameter concerning the first points of a first tridimensional meshing of the points of the object whose cartesian coordinates are generally evenly distributed, this firstly consists of defining second and third points which constitute a second and third tridimensional meshing of characteristic points, the spherical coordinates of the second points being evenly distributed and the second points belonging in particular to the meridian planes converging on an axis, the third points, whose cylindrical coordinates are evenly distributed, belonging both to the meridian planes and parallel planes containing the first points and orthogonal to the axis; then of obtaining information concerning the second points and of calculating derived information; then of combining this information concerning groups of second points belonging to the same meridian planes so as to deduce from this intermediate information concerning the third points; and finally of combining the intermediate information concerning groups of third points belonging to the same parallel planes so as to deduce from this the parameter concerning the first points.

BRIEF DESCRIPTION OF THE DRAWINGS

The invention may be more readily understood by reading the following annexed figures, which are in no way restrictive.

DESCRIPTION OF THE PREFERRED EMBODIMENTS

Figure 1:
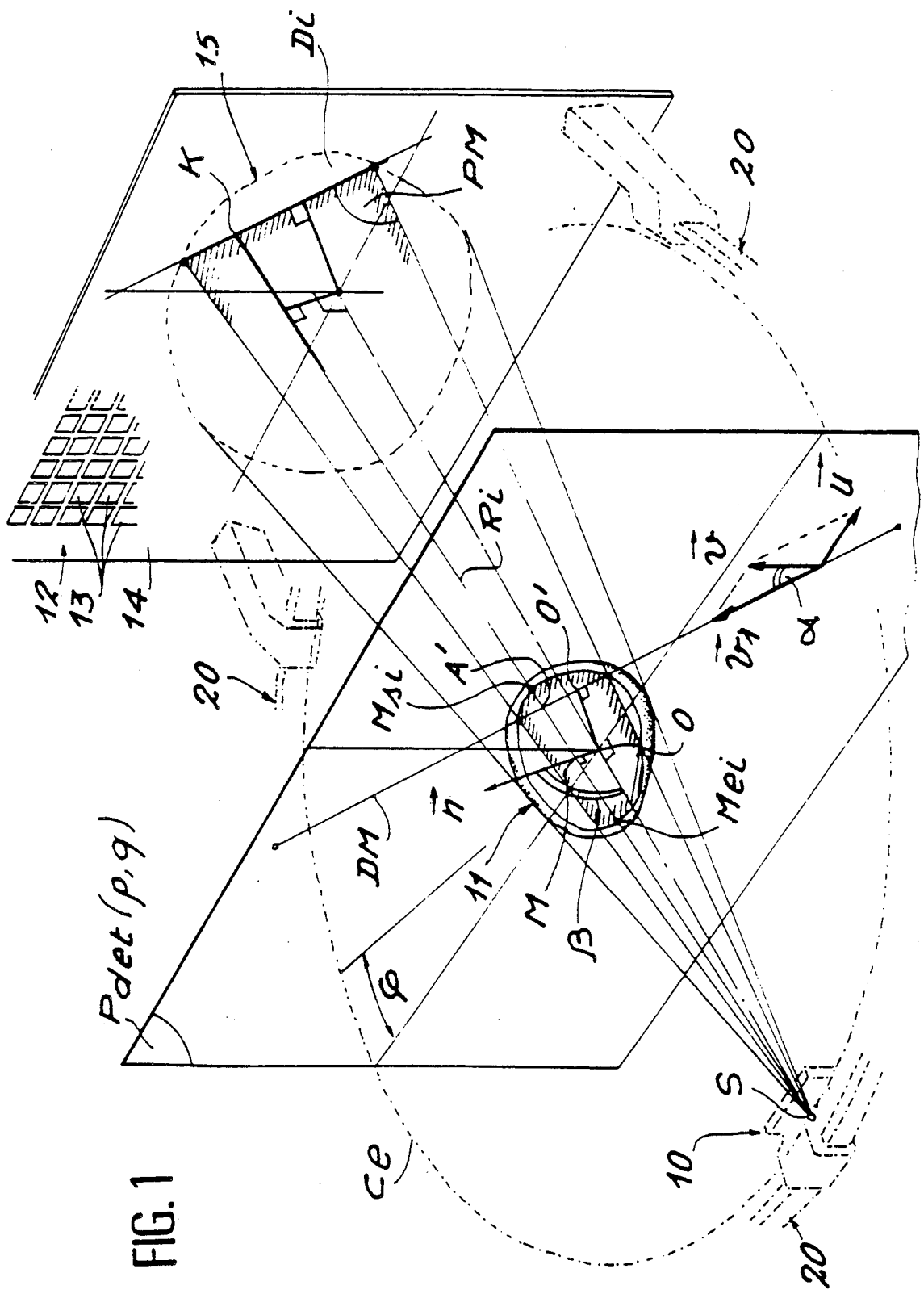
FIG. 1 shows the main parts of a device according to the invention, as well as the notations used for explaining the method.

The device according to the invention comprises (refer to FIG. 1) a source 10 emitting a divergent conical beam whose focal spot is S-shaped and which traverses with attenuation an object 11 to be analyzed and for which it is desired to reconstruct the local contributions upon attenuation. The nature of the radiation may be any, such as X-rays, provided it is able to characterize an element of the object 11 for which it is desired to diagnose the presence or concentration of said element by an attenuation different from the one carried out by its other elements.

An individual ray Ri traverses the object 11 between the input points Mei and output points Msi; in particular, it traverses any supposed intermediate point M and which will serve as a base for the radiations to which it will be exposed. It finally reaches a detector 12 and affects a particular sensor 13 from amongst those of a bidimensional network on a screen 14 situated at a point K. It is marked by the coordinates (p,q) of its track A on a detection plane passing through an origin 0 orthogonal to OS and referenced Pdet on FIG. 1: this immaterial plane is introduced so as to allow for a simpler explanation of the reconstruction method without it being necessary to take account of the remoteness of the screen 14 and its eventual curve.

If the local contribution at the point M upon attenuation of the radiation is noted f(M), the sensor 13 thus measures a radiation intensity:

$$I1 = I0 \exp\left[\int_{Mei}^{Msi} f(Mi)dMi\right]$$

attenuation being supposed negligible outside the object 11 and IO being the known and fixed intensity of the radiation Ri which would have been measured in the absence of the object 11.

IO may also be supplied by a monitoring method evaluating the direct flux on sensors 13 of the bidimensional network or the flux localized outside the measurement field in contact with the object 11 at the output of the source 10.

After logarithmic conversion, a measurement is thus made of attenuation of the radiation through the object along the ray Ri derived from S and passing through A (stage 101 of FIG. 10):

$$\int_{Mei}^{Msi} f(Mi)dMi = X(S, A)$$

Sampling coefficients, calculated in an initial phase during measurements concerning the objects whose attenuation is known, make it possible to correct the data supplied by the sensors.

A bidimensional image 15 is obtained of the object 11 on the screen 14. Conventional radiography is formed by such an image. In order to obtain tridimensional reconstruction, it merely needs to print a rotating movement of the focal spot S of the source 10 around the object 11, for example on a circle Ce centered on the origin O around the object 11 so as to irradiate it under the different incidences and then of combining between them the representations obtained. It is clearly necessary that the detector 12 follows the movement of combining between them the representations obtained. It is clearly necessary that the detector 12 follows the movement of the beam. Here, it is supposed that it also moves on the circle Ce. It may also move in another way, for example on another circle centered on the origin O, but of a different diameter; only the increase in size of the image 15 is different. The trajectory along the circle Ce may be realized by hooking the source 10 and detector 12 to a circular rail 20 whose diameter may be equal or different from that of the circle Ce according to the hooking mode adopted.

However, one major problem appears: as the volume of information to be quickly stored is quite considerable, numerical resolution of the reconstruction problem would need to resort to using complicated matrix calculations. However, the invention does not need to resort to this type of method.

First of all, the transformed Radon from attenuation f(M) of the radiation is defined for those planes passing through a point M (Rf(M)) which defines all the sums of the function describing the local contribution on attenuation of the radiation at their points on each of these planes; these planes are each characterized by a pairing $(\overrightarrow{OM}\cdot\vec{n}, \vec{n})$ where n is a unitary vector perpendicular to the plane in question and $\overrightarrow{OM}\cdot\vec{n}$ is the algebraic measurement associated with the distance of the plane to the origin O. In order to identify these planes, a characteristic point C is used, an orthogonal projection of the origin O on the plane:

$$OC = (\overrightarrow{OM}\cdot\vec{n})\vec{n}.$$

Next, the first derivative of the transformed Radon of attenuation f(M) of the radiation is defined for those planes passing through a point M (R'f(M)) which is equal by definition for each plane P $(\overrightarrow{OM}\cdot\vec{n}, \vec{n})$ to the sum concerning all the points of the plane of the derivative of the function describing the local contribution on attenuation with respect to the direction of the vector n.

Amongst all these planes, it is possible to distinguish and note via the abbreviation PM a Radon plane P IOM.n, n) associated with a characteristic point CM. $\vec{n}$ is defined in a marking linked to the object 11 by its longitude $\phi$ measured in the plane of the circle Ce and by its colatitude $\theta$ measured with respect to the axis of the circle Ce so that $\theta = \tau/2$ when n belongs to the plane of the circle Ce and $\theta = +O$ or $+\tau$ when it is perpendicular to this plane.

In order to determine the values of the transformed Radon Rf(M) or of its first derivative R'f(M) at the point M, it is necessary to especially calculate the sum of the function describing the local contribution on attenuation f(M) or its derivative concerning all the points of the Radon plane PM associated with this point M. This is possible if the focal spot S of the source 10 itself belongs to the Radon plane PM, since one fraction of the radiation or its close proximity does not then leave this Radon plane PM or its close proximity and thus may not undergo attenuation by points of the object to consider this fraction in order to evaluate the sum of the function describing the local contribution on attenuation or of its derivative concerning all the points of the object 11 belonging to the Radon plane PM (the ambient air is virtually not absorbent. If the object of interest is contained in an absorbent environment, the outer environment shall be regarded as a disturbing factor).

However, calculation of the transformed Radon Rf(M) may thus only be made approximately. The Applicant showed that the first derivative of the transformed Radon R'f(M) may on the other hand be calculated exactly, which results in improved quality of the tridimensional images.

Figure 4:
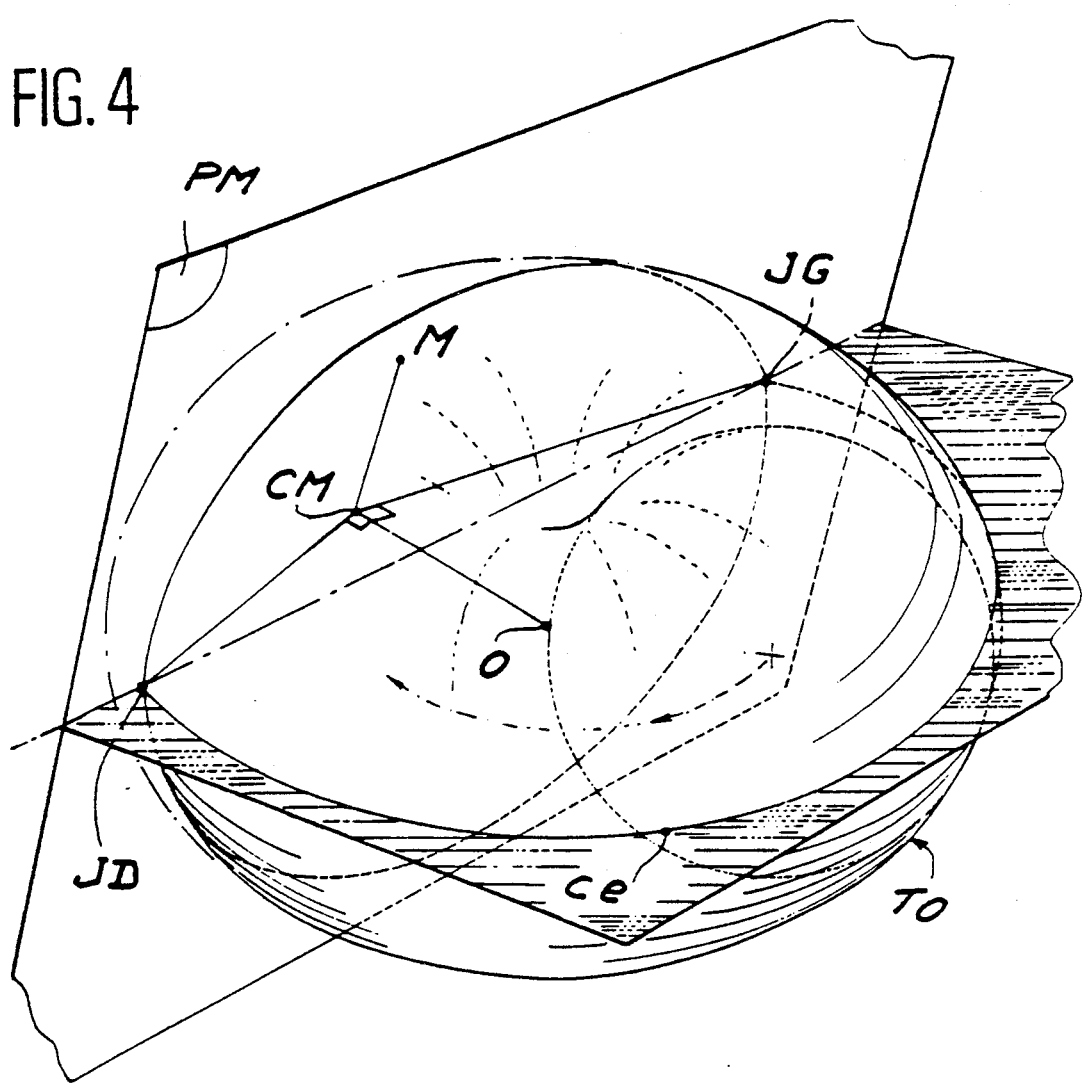
FIG. 4 represents a geometric construction which illustrates one stage of the method according to the invention.

In the case of a source 10, whose focal spot S rotates around the object 11 along a circle Ce, FIG. 4 shows a point M whose Radon plane PM cuts the circle Ce at two points JG and JD. The focal spot S of the source 10 must therefore be placed at one of these points in order to make it possible to calculate the sum of attenuation or its derivative on the Radon plane PM.

The first derivative of the transformed Radon R'f of the object itself is defined as all the summations concerning the Radon planes PM passing through at least one point M of the object of the derivative along the normal vector $\vec{n}$ of the function describing the local contribution on attenuation. The Radon plane PM is common to all the points of the object 11 it contains and in particular to the characteristic point CM. Associated to this point here is the value of the transformed Radon Rf(M) or its derivative R'f(M) on the plane PM.

The characteristic volume of the object refers to all the characteristic points CM associated with all the Radon planes PM passing through at least one point M of the object. The reconstruction of the tridimensional image may be carried out when attenuation is available for all these planes.

However, the measurements only permit access to one value of R'f for the planes PM encountering the trajectory passed through by the focal spot S. The characteristic volume of the measurements refers to all the characteristic points CM associated with the Radon planes passing through at least one point of the trajectory. The characteristic volume of the object must as far as possible be included in the characteristic volume of the measurements.

In the case of a spherical object centered on the origin O and with the radius Rob and the circular trajectory Ce, the characteristic volume of the object is the same sphere centered on O and with the radius Rob. The characteristic volume of the measurements is a torus To shown on FIG. 4 and obtained by the rotation of a circle contained in the plane passing through the focal spot S and the axis of the circle Ce targeting the axis at the level of the origin O and diameter SO.

Thus, it can be observed that the characteristic volume of the measurements does not make it possible to cover the entire characteristic volume of the object: there remains a characteristic shadow zone of the planes encountering the object, but not the circle Ce. The calculation of R'f concerning this zone may only be carried out by interpolation.

Irrespective of the position of the object, there will still be a shadow zone linked to the planes passing through the object, but do not encounter the circle Ce. In order to fill up this shadow zone, it is necessary to renounce the plain circular trajectory and select a trajectory so that any plane passing through at least one point of the object encounters the trajectory.

This condition may be concretely satisfied if the circular trajectory Ce is produced by the accompanying movement of the source 10 and the detector 12 along a circular rail 20 and if associated to (FIG. 2) said rail 20 is a mechanism 21 for pivoting an angle $\xi$ along an axis passing through the origin O thus enabling it to assume two positions materialized by the circles Ce1 and Ce2.

A blocking may be provided by any suitable means for these two positions. This can be easily realized when the nearer the angle $\xi$ is to $\tau/2$, the more the maximum radius Rob of the object sphere centered on O, whose characteristic volume does not have any shadow zone, increases. For $\xi$ being worth $\tau/2$, that is for two perpendicular trajectories, the maximum value for Rob is Rc/$\sqrt{2}$ if Rc denotes the radius of the circles Ce1 or Ce2.

Figure 3:
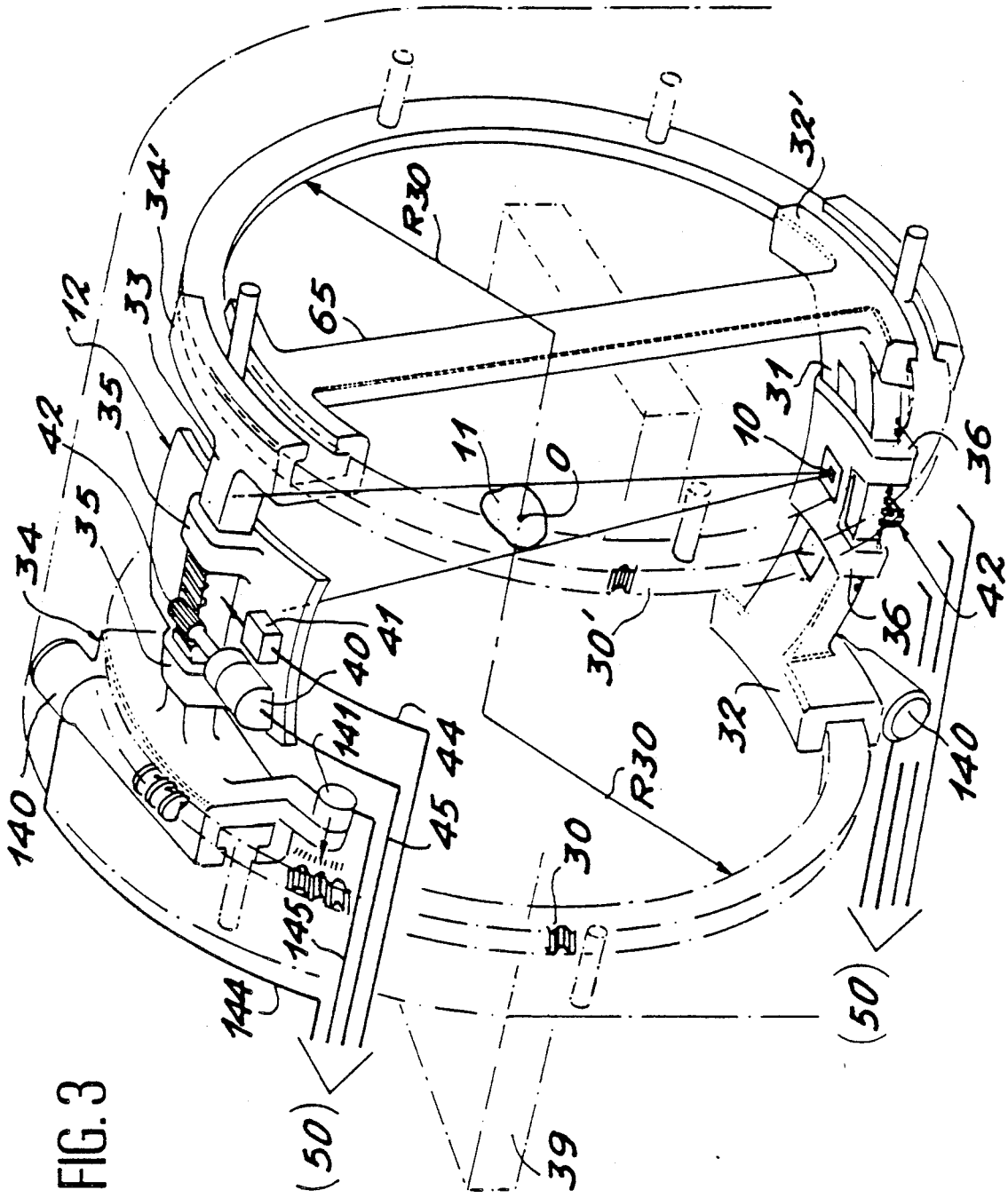
FIG. 3 shows a possible third device according to the invention.

FIG. 3 shows another possibility for embodying such a trajectory: the device here comprises two circular parallel rails 30 and 30' with the same radius R30 each passed through by two diametrically opposed supports 32 and 34 and 32' and 34' respectively. The supports 32 and 32' constitute the extremities of a section 31 along which the source 10 slides by means of handles 36; similarly, the supports 34 and 34' constitute the extremities of a section 33 along which the detector 12 slides by means of handles 35. The sections 31 and 33 are the arcs of circles centered on the origin O.

Thus, it is possible to combine two rotations for the source 10 and the detector 12 in order to replace them concerning trajectories belonging to two concentric spheres. Subsequently, we suppose them to be identical.

Figure 6:
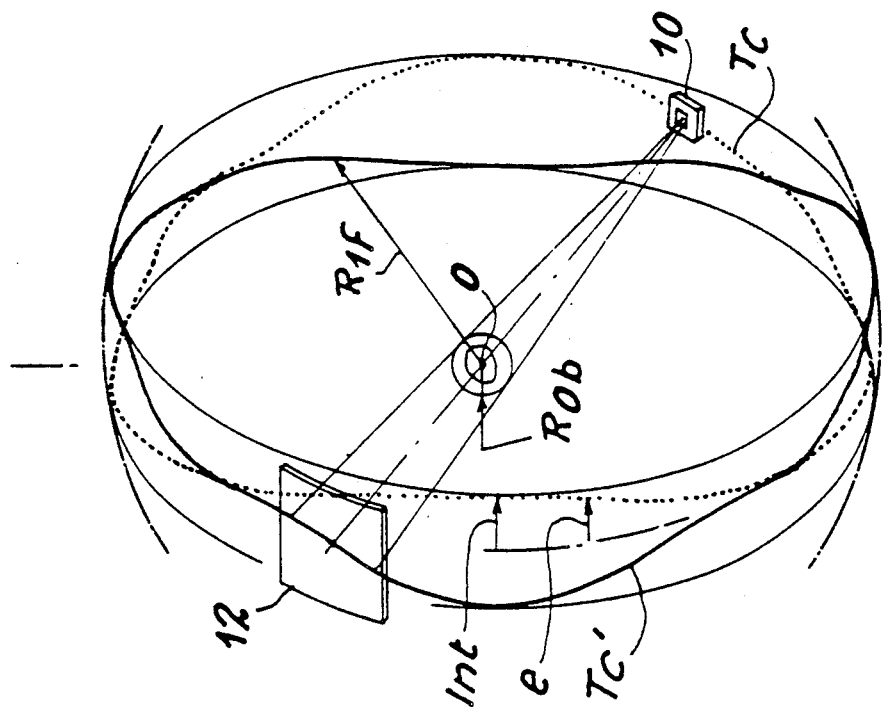
FIG. 6 essentially represents an advantageous double trajectory for conducting analyses by means of the device of FIG. 3.

One possible example is the one where the focal spot S of the source 10 passes through a trajectory Tc shown on FIG. 6 and with an equation $e = Int.\cos2\psi$ where $\psi$ denotes an angle of rotation along the rails 30 and 30', e a clearance parallel to the axis of the rails 30 and 30' with $e=0$ when the focal spot belongs to the plane passing through the origin O and parallel to the rails 30 and 30' and Int is one amplitude. It is then possible to show that the transformed state of Radon Rf(M) or its derivative R'f(M) can be obtained for all the characteristic points CM of the object 11 if $R1f \geq Int.\sqrt{3}$ and $Int \geq Rob$ where R1f is the radius of the smallest sphere centered on the origin O and containing all of the object 11.

During displacement of the source 10, the point of attachment of the detector 12 moves at the same time onto the points of a trajectory Tc' symmetrical with respect to the origin O.

Figure 2:
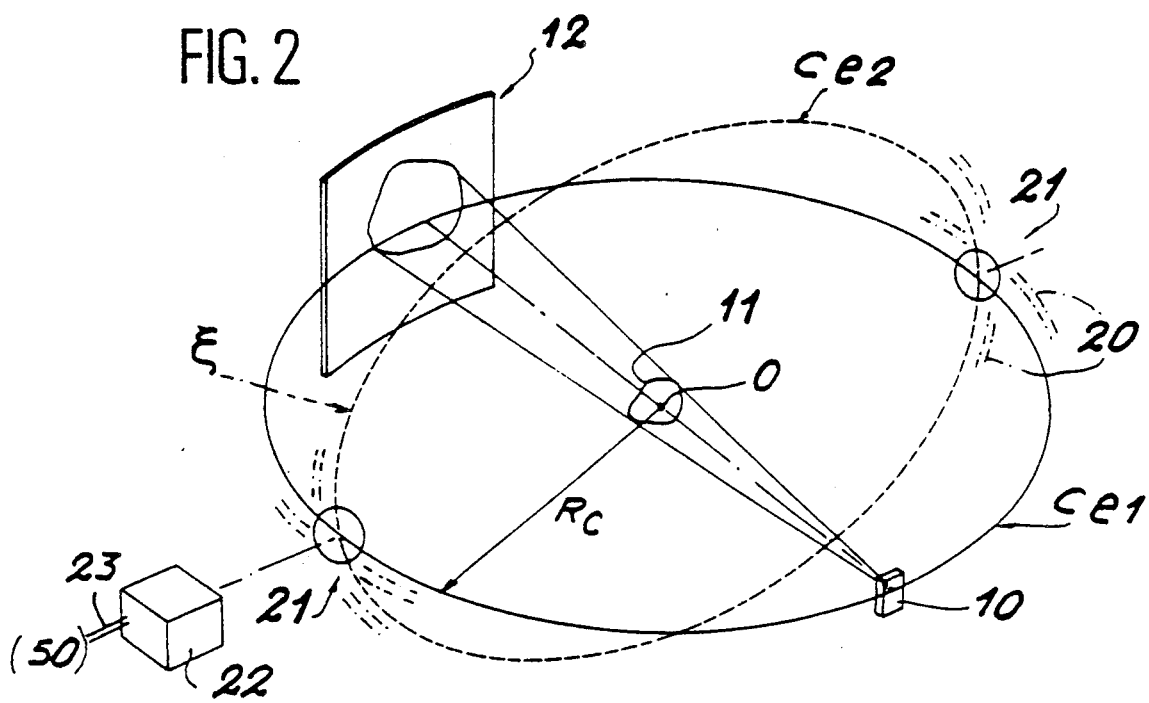
FIG. 2 shows a possible second device according to the invention.

The advantage of the device of FIG. 3 with respect to that of FIG. 2 is to allow for the carrying out in one continuous rotation of the measurements at the time the double circular trajectory imposes a double rotation and a stop time for pivoting and similarly for a given procession speed an examination time at least twice longer. Moreover, the circular double trajectory introduces significant redundancy in the measurements since there is a high proportion of planes which encounter both of the two trajectories. One alternative to the device of FIG. 3 consists of providing the points 21 of FIG. 2 with a motor 22 controlled by a computer 50 (FIG. 7) by means of a line 23 so as to cause the angle $\xi$ to vary when the focal spot S moves onto the circle Ce. Any trajectory may be obtained in the tridimensional space. Considering the respective masses of the radiation sources X and bidimensional detectors, such as the luminosity amplifiers, the device of FIG. 3 seems preferable.

FIG. 3 also shows the device which controls the movement of the detector 12 on the section 33. It comprises an electric motor 40 connected to a computer 50 (FIG. 7) via a line 44 and whose shaft is ended by a gear 42 which gears inside a rack side of the section 33; as the movements require great accuracy, another side of the section 33 comprises graduations 43 marked by an optical sensor 41; it then sends a signal to the computer 50 via a line 45 and stopping of the motor 40 is controlled by the line 44. An identical motor and optical sensor also control the movement of the source 10 on the section 31; on the other hand, there are similar devices with an electric motor 140 and an optical sensor 141 respectively connected to the computer 50 by lines 144 and 145 in order to move the supports 32, 32' and 34, 34' along the rails 30, 30' which thus also comprise a rack and graduations.

The devices of FIGS. 1 and 2 may all also be piloted by these devices although these have not been represented here.

The movements of the source and the screen may generally be independent and synchronized; they may also be obtained by means of a single motor and a mechanical linking effected, for example, by a bar or, more generally, a rigid mechanical structure.

In order to examine the object 11, other devices are also possible.

Figure 8:
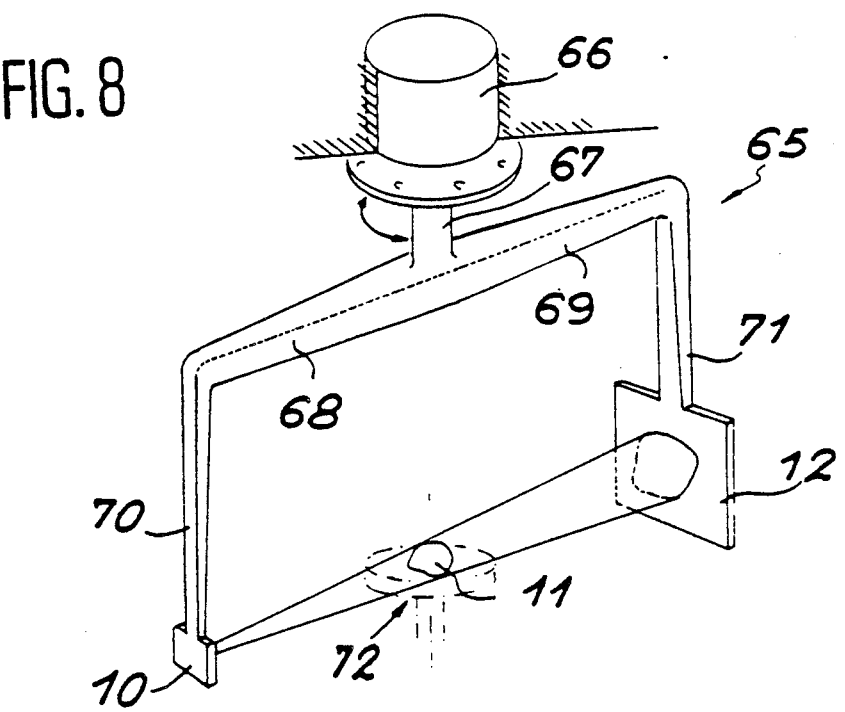
FIGS. 8 and 9 represent two other devices according to the invention.

Firstly, as shown on FIG. 8, it is possible to envisage a device involving a joint movement of the source 10 and the detector 12 connected by a rigid mechanical structure 65 rotating under the action of a motor 66 controlled by the computer 50 around the object 11. This structure comprises a vertical column 67 which is also the output shaft of the motor 66 and from which project are two opposing radial arms 68 and 69. The first arm 68 terminates by a first pole 70 to which the source 10 is suspended, the second arm 69 by a second pole 71 to which the detector 12 is suspended. In this embodiment as in the previous embodiments, the object 11 is laid on a support transparent to radiation and shown here by 72.

Figure 9:
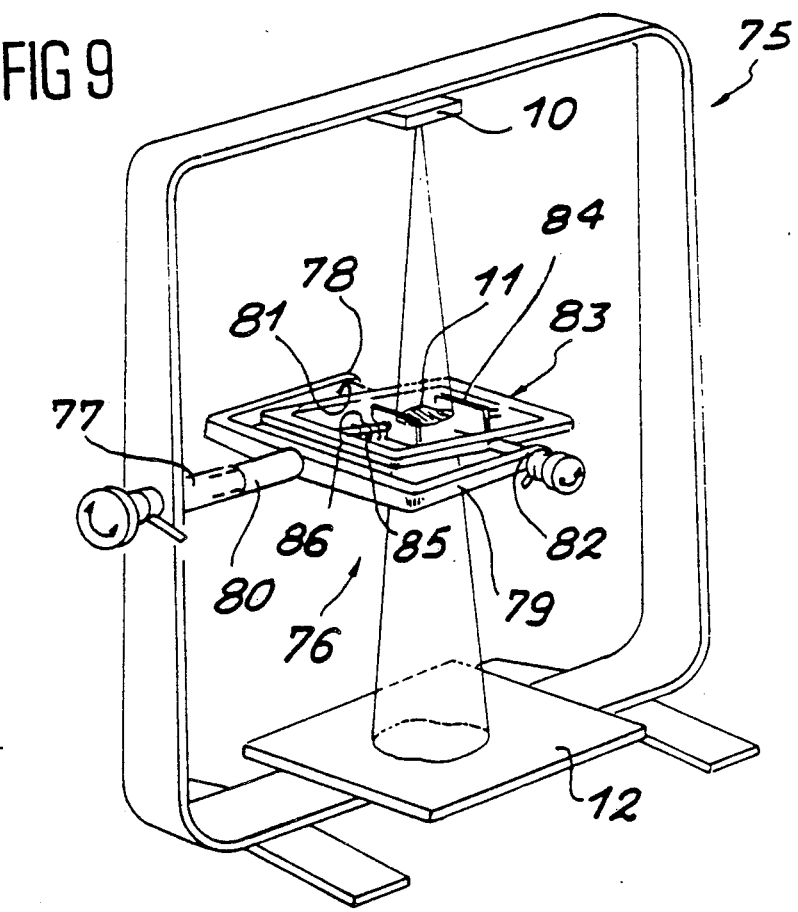

As shown by FIG. 9, it is still possible to apply the invention to a device in which the source 10 and the detector 12 are fixed and hooked to an immobile structure 75 and, on this figure, are shown respectively at the top and bottom of the object 11.

The object 11 is moved in rotation by means of a fork 76 whose sleeve 80 rotates inside a bearing 77 provided inside the structure 75 around an axis roughly perpendicular to the radiation emitted by the source 10. Two bearings, referenced respectively as 81 and 82, are provided inside the two branches 78 and 79 of the fork 76 and receive two pivot pins situated on both sides of a flat frame 83 which thus rotates between the two branches 78 and 79 around an axis perpendicular to the axis of rotation of the fork 76.

The object II is rigidly secured, for example by compression, between two compression plates 84 at one The object 11 is rigidly secured, for example by compression, between two compression plates 84 at one extremity of telescopic rods 85, the other extremity being integral with the frame 83; the telescopic rods 85 have a common directrix and spread towards each other and are pushed by springs 86 around or inside the rods and are compressed between the frame 83 and the compression plate 84 respective to the frame 83. Thus, it is possible to submit it to any rotation and carry out the same examinations as with the other devices described up until now. The compression plates and possibly the rods are assumed to be transparent to radiation from the source 10.

The rotation movements of the fork 76 and the frame 83 are controlled by the computer 50 by means of motors (not shown).

This device is not suitable for the examination of a human being, but is of interest for the nondestructive examination of small objects. However, it is necessary to limit the rotations so as to avoid radiation traversing the frame 83 and the branches 78 and 79 or to also suitably provide these parts in a transparent material.

In order to describe the method for reconstruction of the image by means of the derivative R′f of transformed Radon, new notations (figure I) need to be defined. Reference is made to the detection plane Pdet associated with the position of the focal spot S of the source 10, the plane being perpendicular to the axis $\overrightarrow{OS}$ and passing through the origin O. This plane is provided with a Cartesian mark $(\vec{u},\vec{v})$ so that the mark $$\left(\vec{u}, \vec{v}, \frac{\overrightarrow{OS}}{\|\overrightarrow{OS}\|}\right)$$

is direct. The vector u is selected parallel to the plane of the circle Ce. This detection plane Pdet serves to define the coordinates p and q of the sensors 13 on the detection screen 14. The summation straight line denoted as $D(\overrightarrow{OM}.\vec{n},\vec{n})$ or DM is the intersection of the Radon plane P(OM.n,n) or PM associated with the point M with the detection plane, and 0' being the point of DM, an orthogonal projection of the point O on the straight line DM. The straight line DM is orientated by a unitary vector $\overrightarrow{V1}$ so that:

$$\left(\vec{n}, \vec{v1}, \frac{\overrightarrow{O'S}}{\|\overrightarrow{O'S}\|}\right)$$

forms a direct mark. This is called the angle between the values $\vec{v}$ and $\vec{v1}$.

It is also necessary to define the two weighted attenuation functions:

$$Y(S, A) = X(S, A) \cdot \frac{Rc}{SA}$$

$$Z(S, A) = X(S, A) \cdot \left(\frac{Rc}{SA}\right)^3$$

where Rc is the radius of the trajectory on which the focal spot S moves from the source 10, namely the distance OS. These functions are independent of the Radon plane in question.

Associated to them for each straight line DM are the functions SY(S,M) and SZ(S,M) respectively representing the entirety of the functions Y and Z on the summation straight line.

This shows, which is the start point of the numerical calculations, that:

$$\frac{\|\overrightarrow{OS}\|}{\|\overrightarrow{OS}\wedge\vec{n}\|} \cdot SZ(S,M) \approx Rf(M) \quad (1)$$

$$\frac{1}{\|\overrightarrow{OS}\|} \cdot \frac{\delta SY(S,M)}{\delta\beta} = -R'f(M) \quad (2)$$

where β represents the angle between the vectors $\vec{n}$ and $\overrightarrow{OS}$.

The first formula (1) is an approximate relation linking the measurements to the transformed Radon Rf. The second (2) is an exact relation linking the measurements to the first derivative of the transformed Radon R′f; it makes it possible to obtain more precise results and remains verified irrespective of the distance between the source 10 and the object 11. It thus enables it to be brought together to the maximum, whilst the approximation of the formula (1) is that much more accurate when the source 10 is distanced from the object 11, which imposes the use of an awkward-shaped device.

The formula (2) is mathematically equivalent if the following is posed:

$$Y'(S.A) = \cos\alpha \frac{\delta Y(S.A)}{\delta p} + \sin\alpha \frac{\delta Y(S.A)}{\delta q} \quad (3)$$

with the two formulae:

$$R'f(M) = \frac{\|\overrightarrow{OS}\|^2}{\|\overrightarrow{OS}\wedge\vec{n}\|^2} \cdot \frac{1}{|\sin\alpha|} \cdot \int_{p=-\infty}^{+\infty} Y'(S.A(p))dp \quad (4)$$

$$R'f(M) = \frac{\|\overrightarrow{OS}\|^2}{\|\overrightarrow{OS}\wedge\vec{n}\|^2} \cdot \frac{1}{|\cos\alpha|} \cdot \int_{q=-\infty}^{+\infty} Y'(S.A(q))dq \quad (5)$$

where A(p), respectively A(q) represent the point A of the summation straight line DM of absciss p respectively of ordinate q.

Preferably, the formula (5) is selected for α close to O modulo τ and the formula (4) is selected for c close to τ/4 modulo τ.

Figure 10:
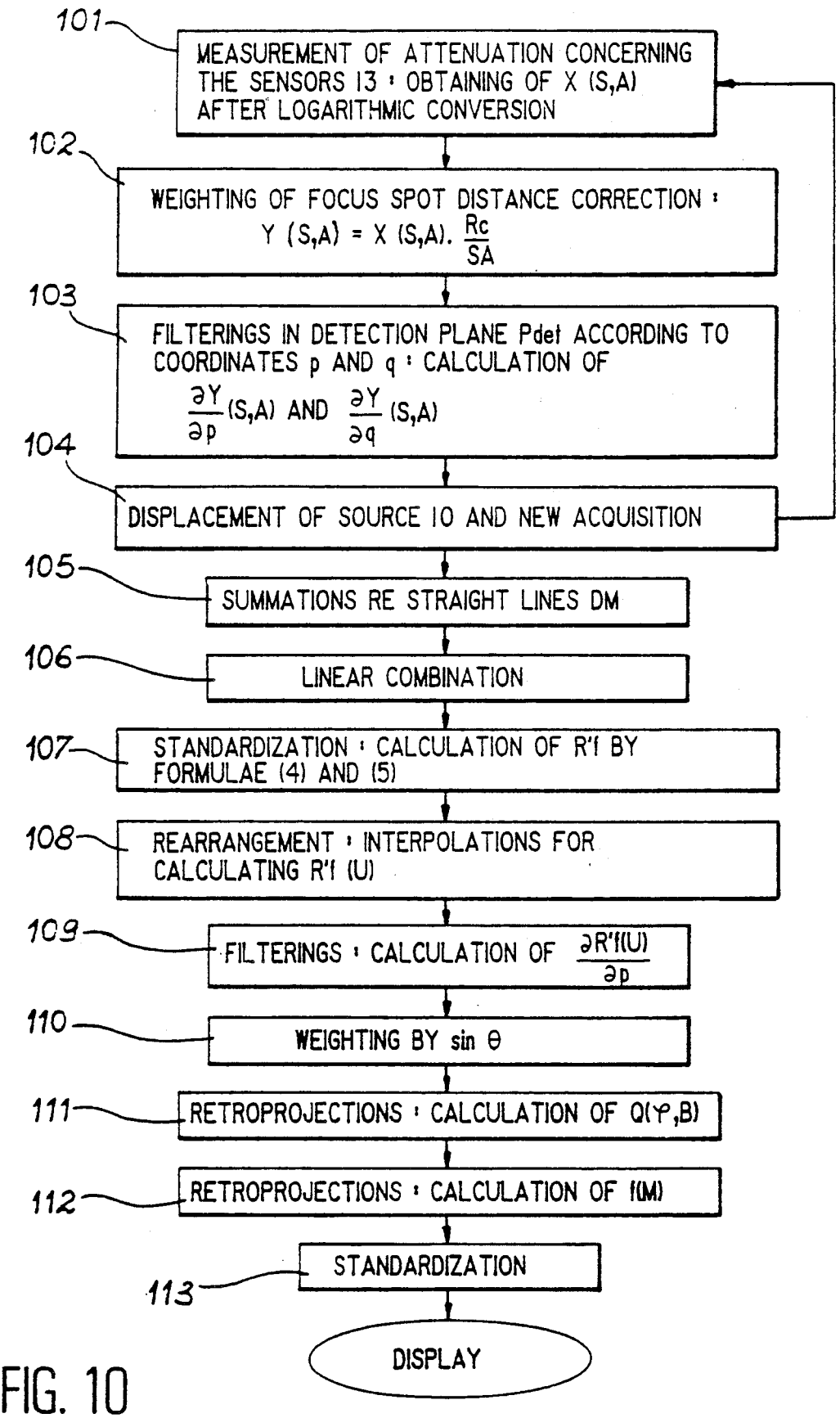
FIG. 10 shows a flowchart of the method used.

As shown by the flowchart of FIG. 10, for a given position of the source 10, the quantities X(S,A) and Y(S,A) are thus calculated of any point A of the detection plane Pdet (stages 101 and 102). The derivatives of Y(S,A) with respect to the coordinates p and q of the detection plane Pdet are completed by the filtering operations (stage 103) by using the convolution of the function Y(S,A) by two differentiation filters. The source 10 is then moved as far as its next position (stage 104) and the cycle recommences until all the acquisitions have been carried out.

The subsequent stages consist of carrying out calculations for characteristic points U' of the characteristic volume of the object. These calculations introduce the Radon plane PM which is associated with them, as well as the intersection Radon straight line DM of the Radon plane PM with the detection plane Pdet. Calculation starts as follows (stage 105):
in the case of formula (4):

$$\int_{p=-\infty}^{p+\infty} \frac{\delta Y}{\delta p}(S.A)dp$$

and $$\int_{p=-\infty}^{+\infty} \frac{\delta Y}{\delta q}(S.A)dp$$

and in the case of formula (5):

$$\int_{p=-\infty}^{+\infty} \frac{\delta Y}{\delta p}(S.A)dq$$

and $$\int_{p=-\infty}^{+\infty} \frac{\delta Y}{\delta q}(S.A)dq$$

by summation concerning the Radon straight lines DM and then a linear combination (stage 106) allowing the following to be obtained:
in the case of formula (4):

$$\cos\alpha \int_{p=-\infty}^{+\infty} \frac{\delta Y}{\delta p}(S.A)dp + \sin\alpha \int_{q=-\infty}^{+\infty} \frac{\delta Y}{\delta q}(S.A)dp.$$

and in the case of formula (5):

$$\cos\alpha \int_{q=-\infty}^{+\infty} \frac{\delta Y}{\delta p}(S.A)dq + \sin\alpha \int_{q=-\infty}^{+\infty} \frac{\delta Y}{\delta q}(S.A)dq$$

after which these quantities are standardized (stage 107) by multiplying them by:

$$\frac{\|\overrightarrow{OS}\|^2}{\|\overrightarrow{OS}\wedge\vec{n}\|^2}$$

then by $1/|\sin\alpha|$ or $1/|\cos\alpha|$ respectively. The result is equal to R'f(U).

If the system of coordinates (p,q) is not adapted for fixed sampling by the distribution of the sensors on the detector 12, these formulae may subsequently be transposed into the appropriate system of coordinates. It is also possible inversely to recalculate by interpolating the attenuations into the system of coordinates (p,q), thus carrying out what is called a recorrection or resampling of the measurements.

In the case where a Radon plane encounters the trajectory at several points, for example two (JG and JD) in the case of FIG. 4, it is useful to carry out an average concerning all or at least one part of the values of R'f associated with each of these points so as to reduce the statistical errors linked to noise concerning these measurements. Generally, an average is nevertheless selected relating to two preferential points.

In the case where a Radon plane associated with a characteristic point CM does not encounter the trajectory at any point, which occurs if the characteristic volume of the measurements leaves a shadow zone within the characteristic volume of the object, it is desirable that it be nevertheless allocated a value R'f via an interpolation procedure. In order to do this, it is possible, for example, to set up an interpolation of about zero: associated with the characteristic point CM, outside the characteristic volume of the measurements, is the surface corresponding to the intersection of the sphere centered on O and passing onto CM with the characteristic volume of the measurements. Then on this surface, a point C'M (not shown) is selected at a minimum distance from CM. By definition of the characteristic volume of the measurements, the plane P'M (not shown) admitting as a characteristic point C'M shall encounter the trajectory at one or more points, most of the time remaining as a tangent to these. The preceding method makes it possible to define a value R'f associated with C'M. The approximately zero interpolation consists of allocating this same value to the point CM.

Thus, a value R'f is allocated to all the points of the characteristic volume of the object. As already mentioned, it is of course preferable to avoid interpolation regarding the shadow zone and thus to use a device, such as the one represented on FIG. 3. However, for more mechanical simplicity of the device, it is possible to be satisfied with the simple circular trajectory Ce and tolerate the interpolation in order to fix the values concerning the associated shadow zone.

It merely remains to deduce f(M) from knowledge of the first derivative R'f of the transformed Radon concerning the object characteristic volume. This inversion operation is straightforward and can be implemented by high-capacity calculations.

For a given unitary vector $\vec{n}$, the algebraic measurement (radius) P is noted of the points U' concerning the origin axis O and directive vector $\vec{n}'$.

The theoretical inversion formula of the first derivative of the transformed Radon R'f is written as follows:

$$f(M) = -\int_{\rho=0}^{\pi}\int_{\theta=0}^{\pi} \frac{\delta R'f}{\delta \rho}(U')\sin\theta d\theta d\rho \quad (6)$$

Note that $\omega$ and $\theta$ denote the longitude and colatitude of the point in question (here U') and $\rho$ is defined by $\overrightarrow{OU'} = \rho.\vec{n}$.

However, it is necessary to look into the rendering discrete problems which have not been mentioned so far in this text.

In particular, it is evident that the source 10 may only carry out exposures under a finite number of determined incidences, that the detection screen 14 carries out the measurements by means of a network of sensors 13 marked on the detection plane as also a finite number, and that the object 11 must be rendered discrete or also meshed.

Inevitably, interpolation problems arise. The recommended solutions and which also belong to the invention are described below. Simultaneously, an examination is made of the conditions relating to resolving the rendering discrete problems so as to enable correct reconstructions to be obtained.

The object 11, assumed to be entirely included in a sphere centered on the origin O and with a radius Rob, may be described with the aid of the points M which result in rendering discrete an even parallelpiped display or representation meshing whose coordinates verify:

$x(i)=[(2i-1-Nx)/Nx].Rob$ where $1 \leq i \leq Nx$, $y(j)=[(2j-1-Ny)/Ny].Rob$ where $1 \leq j \leq Ny$, $z(k)=[(2k-1-Nz)/Nz].Rob$ where $1 \leq k \leq Nz$.

If $\nu$ is the sought-after cut-off frequency for the imagery system 3D, Nx, Ny and Nz are preferably taken as being greater than or equal to $4.\nu.Rob$.

The detection screen 14 is also advantageously graduated in Cartesian coordinates, which moreover have already been introduced. The locations of the sensors 13 defined by their coordinates on the detection plane Pdet verify:

$p(a)=[(2a-1-Np)/(Np-2)/(NP-2)].Rob$ where $1 \leq a \leq Np$, $q(b)=[(2b-1-Nq)/(Nq-2)/(Nq-2)].Rob$ where $1 \leq b \leq Nq.Z$ Np and Nq are equal to or greater than $4.\nu.Rob$.

The points U of the sampling of the first derivative of the transformed Radon are defined with the aid of a spherical meshing (a pattern defining a volume in which points are arranged) centered on the origin O; their spherical coordinates verify:

radius: $p(n)=[(2n-1-Nn)/(Nn-2)].Rrad$ where $1 \leq n \leq Nn$, colatitude: $\theta(l)=[(2l-1)/2Nl].\tau/2$ where $1 \leq l \leq Nl$, longitude: $\phi(m)=[(m-1)/Nm].2\tau$ where $1 \leq m \leq Nm$. where Rrad is the radius of the sphere centered on O encompassing the object characteristic volume. For an object sphere with a radius Rob, Rrad=Rob.

For Nn, an even number is preferably taken so as to not incorporate the origin O in the meshing, as it characterizes an infinite number of planes. On the other hand, the following is chosen:

Nm=2.Nn and Nl=Nn/2 for
$2\tau.\nu.Rob \leq Nm \leq 4\tau.\nu.Rob$.

This makes it possible to reduce the artifacts linked to the inversion of the first derivative of the transformed Radon to an acceptable level.

The positions of the source 10 from which the attenuation measurements are made are the intersections of the meridian planes orthogonal to the meridian planes of longitude (m) with the trajectory Ce or Tc.

The actual problem thus consists of calculating from the Nm positions, which may be assumed by the source 10, the first derivative of the transformed Radon R'f(U) for the entire network of the points U and then the local contribution on attenuation f(M) for the entire network of the points M. This is arrived at with the aid of a series of interpolation stages. One possible method is given in detail in the continuation of this text.

Figure 5:
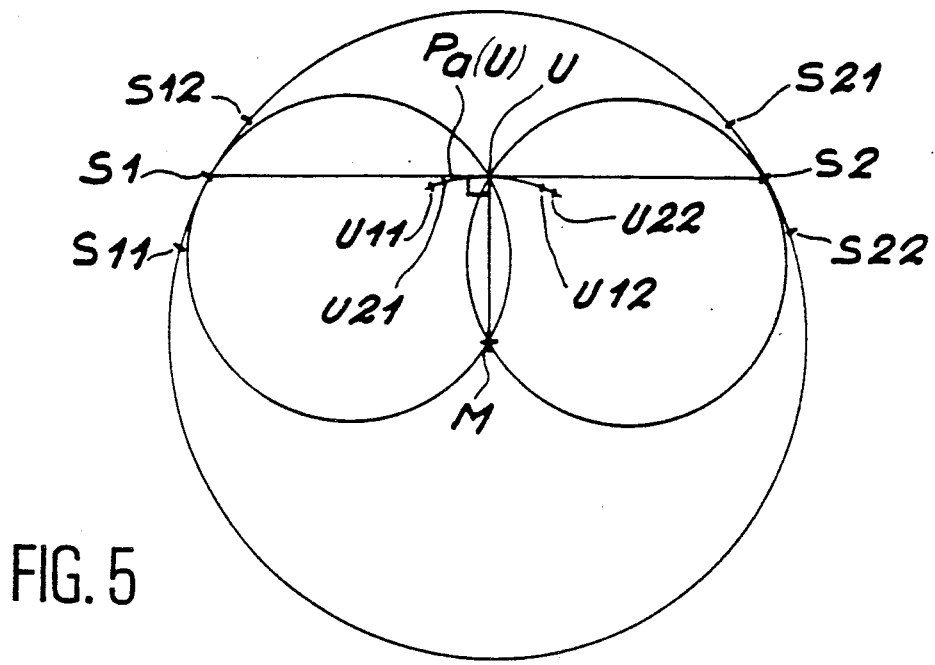
FIG. 5 shows a geometrical construction which illustrates an interpolation stage required for application of the method.

For the points U forming part of the characteristic measurement volume, FIG. 5 shows that the derivative of the transformed Radon R'f(U) of any point U can be obtained for at least two generally different locations S1 and S2 of the focal spot S for which the spheres, whose diameters are limited by the origin O and respectively by the locations S1 and S2, meet at the point U. In practice, the locations S1 and S2 do not, however, correspond to the measurement positions of the focal spot S, but are each situated between two of these positions, namely respectively S11 and S12 and S21 and S22.

For the points U outside the characteristic measurement volume, the source positions S1 and S2 are marked from the point of the characteristic measurement volume used to define the zero order interpolation referred to earlier.

In actual fact, the first derivative of the transformed Radon is calculated for the points U11, U12, U21 and U22 forming part of all the points U' and being the nearest points of intersection of U of spheres with respective diameters of OS11, OS12, OS21 and OS22 with the circle corresponding to the parallel line of the point U (all the points with the same radius (n) and the same colatitude $\theta$(l)). If this intersection is empty, the points of intersection circles are taken between these spheres and the sphere centered on O and passing through the nearest U's of the circle corresponding to the parallel line of the point U. Their distances of the point U are respectively d11, d12, d21 and d22.

The transformed Radon is calculated from the point U or its derivative via the interpolation formula (7):

$$R'f(U) = \frac{1}{2}\left[\frac{d12R'f(U11)d11R'f(U12)}{d11+d12} + \frac{d22R'f(U21)+d21R'f(U22)}{d21+d22}\right]$$

and

This operation corresponds to stage 108 of the flowchart.

It is clear that the computer which manages the process knows in advance the position of the points S11, S12, S21, S22, U21, U12, U21, U22 for any point U of the sampling, as well as the distances d11, d12, d21 and d22 which are stored in the memory; the position of the summation straight lines associated with the points U11, U12, U21 and U22 is also known in advance and the attenuation values X(S,A) along its points are obtained by interpolation of the values measured on the sensors 13 traversed by this straight line. In order to calculate the sum concerning the points in question of any summation straight line, the computer 50 thus possesses weighting coefficients associated with each sensor 13. With the proposed sampling, the points U number $Nl \times Nm \times Nn = Nn^3$ and there are 2.Nn positions of the source 10; for each of these positions, the transformed Radon or its derivative is calculated for $Nn^2$ summation straight lines DM. Then, an average is calculated concerning the values combined two by two.

In order to carry out the numerical calculation of the formula (6), it is possible and advantageous to separate the integrals.

So as to describe the execution of this calculation, the notion of the plane of rearranged projections is introduced passing through the origin O and whose points are at a constant longitude. Thus, this involves meridian planes.

To any point B of this plane and to any vector n with a longitude, the point CB is associated, an orthogonal projection of the point B on the axis passing through the origin O and with a director vector n. When B describes the plane of rearranged projections, the point CB describes a plane of characteristic points corresponding to the meridian plane associated with the longitude $\phi$. Geometrically, these two planes are merged.

It may be noticed that if B is the orthogonal projection of the point M on the plane of rearranged projections, the point CB is identical to the characteristic point CM associated with the plane DM defined by M and n.

It is thus possible to start by calculating concerning each plane of rearranged projections from the values R'f relating to the associated meridian plane the following quantity:

$$Q(\rho, B) = -\frac{1}{4\pi^2}\int_{\theta=0}^{\pi} \frac{\delta R'f}{\delta \rho}(CB)\sin\theta d\theta \quad (8)$$

for all the points B which are orthogonal projections of at least one point M of the object.

Then secondly, the local calculation on attenuation is calculated for each point M of the object:

$$f(M) = \int_{\phi=0}^{\pi} Q(\phi, B)d\phi$$

This method makes it possible to obtain a strict reconstruction of the object 11 even if the characteristic volume of the object is entirely included in the characteristic volume of measurements.

Moreover, the use of the exact formula makes it possible to bring nearer the source 10 of the object 11. Thus, it is possible to reduce the spatial requirement of the device and increase the growth factor (focal spot S distance—detector 12/focal spot S distance—object 11) and thus improve the spatial resolution of the device. Furthermore, this contributes in providing better use of the radiation to the extent that this enlarges the solid irradiation angle of the object. As the radiation sources are limited in their output of photons per angular unit, for a total number of photons required to pass through the object during the period of measurements, this enables the examination time to be reduced and thus to increase temporal resolution. It also, by retaining the same examination time, allows statistical accuracy to be improved as regards the reconstructed object.

The reconstruction diagram may be generalized to a wide class of trajectories by authorizing, for example, that the distance of the focal spot from the source 10 or from the detector 12 is different, indeed even variable. In the preceding formulae, the weighting coefficients linked to growth shall then depend o the measurements.

It should be mentioned that the source 10 and the object 11 may also be brought together if a trajectory is selected according to FIG. 6 and conforms to the formula:

$$e = Int(\cos.n\psi)$$

the higher is n.

Inversion of the derivative of the transformed Radon, defined by the formulae mentioned above, is effected concretely with the aid of the points B of a meshing known as a rearrangement meshing plotted on the planes of rearranged projections associated with the meridians of the points U by way of sampling:

$$r(c) = [(2c-1-Nn)/(Nn-2)].Rrad \text{ where } 1 \leq c \leq Nn,$$

$$z(d) = [(2d-1-Nz)/Nz].Rob \text{ where } 1 \leq d \leq Nz,$$

$$\phi(m) = [(m-1)/Nm].2\tau \text{ where } 1 \leq m \leq Nm,$$

where r(c) denotes the coordinate of a point B of a meridian plane along the axis parallel to the plane of the circle Ce, and z(d) the coordinate of a rearrangement point B along the axis of rotation of the circle Ce: on each meridian plane, the points B are evenly distributed on a rectangular network.

Calculation of the quantity $Q(\psi,B)$, such as the one defined earlier, is thus limited to the calculation of the quantities $Q(\psi,B)$ for the points of the rearrangement meshing after an interpolation has enabled the derivatives $\delta R'f(CB)/\delta\rho$ to be obtained from the derivatives $\delta R'f(U)/\delta'$ for each direction of the meridian (stage 111).

Calculation of the derivatives $\delta R'f/\delta\rho$ shall advantageously have been carried out by digital processing techniques, as for example convolution by the associated filters. The data would have also been firstly weighted by the factor sinθ (weighting and filterings stages 109 and 110).

According to known techniques, the filtering operations linked to the calculation of δR'f/δρ and and the retroprojection operations linked to summation concerning the colatitude θ may be replaced by one retroprojection operation followed by one filtering operation without departing from the context of the present invention. The filtering operation could also possibly be made on the object 11 after summation concerning the angles θ and has been carried out.

The final interpolations to be carried out are made inside each plane of the object perpendicular to the meridian planes: one has seen that the calculation of the local contribution on attenuation f(M) of the point M introduces the orthogonal projections of the point M concerning each rearranged projection plane taken into account. These projections fall between the points B where it is necessary to interpolate the quantities Q(ω, B) before adding them up, thus realizing retroprojection operations (stage 112).

For these final operations, the system is also aware in advance of the positions of the points of the different meshings and possesses, in the form of tables or matrixes, and possesses the coefficients to be taken into account. The prior programming work is thus important and must be repeated if it is desired to have several different samplings, but the calculations to be made during an examination remain reasonable and mainly comprise linear combinations and filterings.

Figure 7:
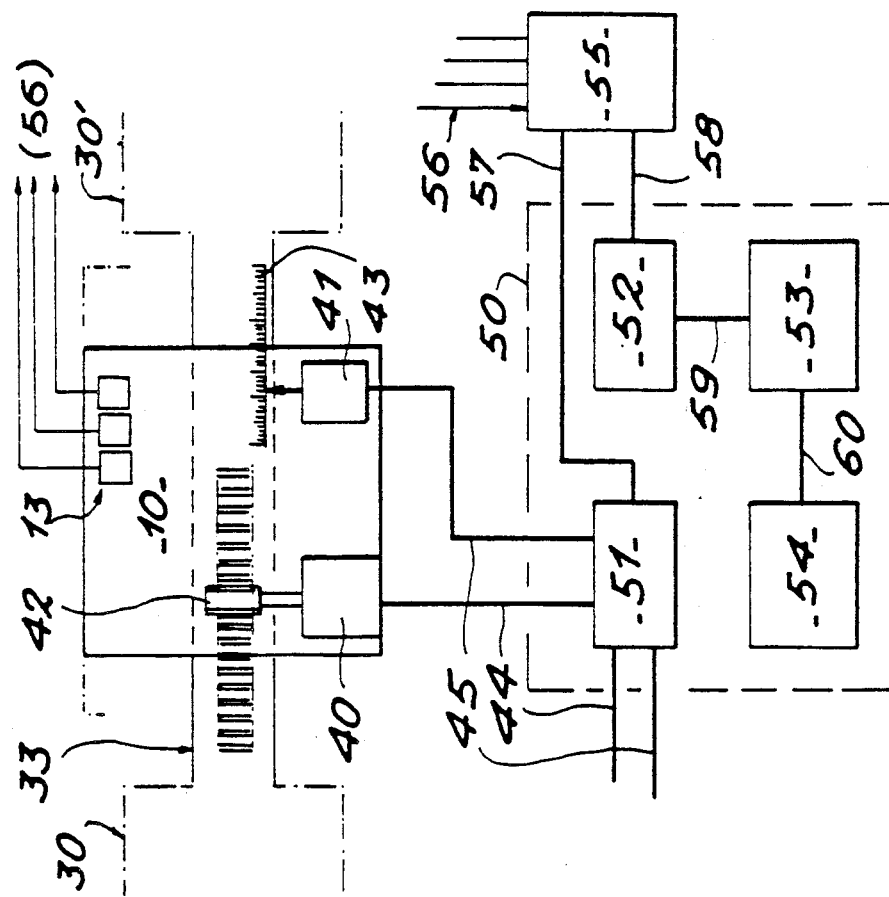
FIG. 7 shows a synoptic diagram of the installation which pilots the devices according to the invention.

A computer 50 manages the reconstruction process (FIG. 7). It consists of a synchronization unit 51, a memory unit 52, a calculation unit 53 and peripheral units 54. Initially, the synchronization unit 51 ensures acquisition of the measurements: according to the indications of the optical sensors 41 or 141, it activates the electric motors 40 or 140 and stops them when the source 10 and the detector 12 are at a predetermined measurement position; then by means of a line 57, it indicates the start and end of the acquisitions on an ordinary chain of measurements 55 connected by a line 56 to each of the sensors 13 whose processed information is supplied by a line 58 to the memory unit 52.

When acquisition is terminated for a given position of the source 10, the synchronization unit 51 restarts the electric motors 40 or 140, whilst the sensors 13 are reset to zero. The next measurement may then be carried out and stored.

It is still possible to continuously move the source 10 and the detector 12. The total time involved in executing the measurements is then appreciably reduced as the motors are no longer stopped, but it is necessary to accept a lack of focus of the image due to rotation during each irradiation.

It should be mentioned that the graduations 43, which indicate the positions of the irradiations on the synchronization unit 51, are not necessary; they can also be eliminated and the synchronization unit 51 itself determines the cycle of irradiations by means of a clock incorporated in the synchronization unit.

After acquisition of all the measurements, the actual examination of the object is completed. All the information passes into the calculation unit 53 via a line 59; the calculation of the transformed Radon or its first derivative is made, as well as their inversion.

The values of the local contribution on attenuation f(M) are finally routed by a line 60 towards the peripheral units 54 which in particular contain graph outputs and display screens.

The differentiation and interpolation operations described here must not be merely considered as calculation tools and may be replaced by other operations without departing from the context of the present invention; similarly, the proposed samplings are merely examples and may vary within relatively wide limits. Several of the operations of the flowchart may also be inverted.

However, it should be noted that the expression of the derivative of the transformed Radon, the circular trajectory and the conical beam, for analytic and numerical precision reasons, virtually impose working with a spherical beam of points U when it is natural to represent an object, even with a quasi-spherical shape, with the aid of a rectangular network of points M in which flat sections may be defined. Several interpolation operations are thus essential so as to pass from one network to the other. On the other hand, the density of the meshing of the points M of the object 11 does not strictly depend on the number of measurements defined by the number Nm: a certain flexibility is thus possible at this level.

It is finally clear that the devices involving movements of the source, object and the detector, said movements being different from those described here by way of illustration, still come within the context of the invention. Similarly, the measurements may be carried out more quickly by several sources functioning simultaneously, the views being distributed between these.

Accordingly, the invention provides an extremely useful method of obtaining tridimensional reconstructions from bidimensional measurements of the attenuation of a radiation. One plausible application is obviously medical imagery and a second is nondestructive control, but any object 11 compatible with the dimensions of the equipment and the radiations available could be examined. The algorithms used directly calculate the solution, which accelerates processings compared especially with iterative methods. Finally, the method guarantees exact localization of the information measured: no distortion of the image appears, which is not the case when an image is made by using other methods of the prior Art.

According to the measurement device and the conventions used, different standardization factors or scale changes may be made (stage 113 of the flowchart). The local contributions on attenuation described in the text correspond to linear coefficients of attenuation. But it also possible, for example, to express the attenuation measurements as a length of equivalent water, and then after reconstruction translate the result of the calculations by using the Hounsfield scale according to the conventions for medical scanners X.

I claim:

1. A device for obtaining tridimensional images from bidimensional measurements of the attenuation of radiation through an object comprising;

a radiation source for irradiating a conical space from a focal spot (S) in which the object is placed;

a detector comprising a bidimensional device for measuring the attenuation of the radiation through the object, a mechanism for performing a series of measurements under different incidences, as well as a chain or measurements; and a computer for the analysis and processing of the information of the bidimensional device at the time of the measurements and for calculating from the local radiation contribution f(M) at different points (M) of a meshing representing the object upon attenuation of radiation, wherein the source is unique and the computer comprises units for performing the calculation and inversion of the derivative of the transformed Radon of attention of radiation, a mathematical function called a Radon transform of a function being defined as all the local values of this function concerning each plane passing through at least one point of the range where the function is defined, and the derivative of the transformed Radon being defined as the sum of the variation rates on each of said planes if movement occurs perpendicular to said plane in the direction of the normal vector defined by a system of spherical coordinates and wherein the derivative of said transformed Radon is used for constructing an object.

2. A imagery device according to claim 1, wherein the source and detector are fixed at a constant distance from a fixed origin for the various incidences.

3. A device according to claim 2, wherein the mechanism comprises a circular rail centered on the origin (O) for guiding the source and the detector during the measurements so that they remain in a fixed alignment with the origin (I) at a constant distance, with the source's movement describing a circular trajectory Ce.

4. A device according to claim 3, wherein the circular rail further comprises a pivot for enabling the source to be moved according to two circular trajectories (ce1, Ce2) offset from a constant angle ($\xi$), 5. A device according to claim 3, wherein the circular rail further comprises a pivot for controlling by a motor which is controlled by the computer enabling said motor to undergo a time-controlled variable rotation.

6. A device according to claim 2, wherein the mechanism further comprise:

two parallel circular rails, made up of two sections on which slide respectively the source and the detector said sections both being placed such that they are at opposing positions with respect to the origin(O) and such that said source and said detector transverse the circular rails so when a measurement is carried out, the sections moreover are bent back as an arc of a circle so that their points are at a constant distance from the origin (O), such that the source and the detector can remain permanently aligned and at a constant distance from the origin (O).

7. A device according to any one of claim 3 to 6, further comprising rials on which the source and the detector (12) move by means of electric motors piloted by the computer with the aid of marking devices.

8. A device according to claim 6, further comprises means to move said sections on said circular rails by means of electric motors piloted by the computer (50) with the aid of marking devices.

9. A device according to claim 2, wherein the source and the detector are connected by a rigid mechanical structure.

10. A device according to claim 9, wherein the rigid mechanical structure pivots around an axis passing through the origin (O).

11. A device according to claim 9, wherein the rigid mechanical structure is immobile and includes another mechanical structure to which the object is secured and which enables it to carry out rotations according to at least one axis passing through the origin (O).

12. A method for the tridimensional optical image formation of an object for bidimensional measurements of the attenuation of a radiation through the object by using a device formed from a conical radiation source comprising a focal spot (S) and a bidimensional detector formed from a network of sensors (13), wherein in each of the first points (M() of a discretization representing the object, the attenuation of the radiation f(M) is calculated by calculating quantities (R'f(U)) representative of the derivative of the transformed Radon of attentuation of the radiation of the points (U) of a second meshing of the object, the transformed Radon of a function being defined as all the local values of this function concerning each plane passing through at least one point of the range where the function is defined, and the derivative of the transformed Radon being defined as the sum of the variation rates concerning each of said planes if movement occurs perpendicular to said plane in the direction of the normal vector defined by a system of spherical coordinates, the quantities (R'f(U)) being calculated by carrying out the summation for each second point (U) of the variation of attenuation of the radiation along at least one line obtained by the intersection of the detector with a plane passing through the focal spot (S) of the conical radiation in the proximity f the second point (U), the straight line passing through the focal spot (S), then linear combinations of these summations, and the attenuations of the radiation at each of the first points (M) being obtained by derivation of these quantities with respect to the distance to the origin (O), and by linear combination of the derived quantities, interpolations being moreover carried out so as to pass from the second points (U) to the first points (M) such that an object can be constructed.

13. A tridimensional optical image formation method according to claim 12, wherein the quantities (Ff(U)) are each determined by summation of the variation of the attenuation along lines obtained by the intersection of the detector and planes each passing through an interpolation point (11, U12, U21, U22) close to the corresponding second point (U), as well as through different positions of the focal spot (S) of the conical radiation, the straight line defined by the original (O) and each interpolation point (U11, U12, U21, U22) being orthogonal to the plane passing through said interpolation point.

14. A tridimensional optical image formation method according to either of claims 12 or 13, wherein the measurements are carried out when the focal spot (S) of the conical radiation occurs on meridian planes distant from regular angles ($2\tau/Nm$) and converging at an axis passing through the origin (O).

15. A tridimensional Tridimensional optical image formation method according to claim 14, wherein the source and the detector transverse two trajectories (Tc, Tc') at a constant distance from the origin (O) roughly in the shape of a sinusoid comprising at least two periods over a complete revolution around the object.

16. A tridimensional optical image formation method according to claim 14, wherein the source and the detector transverse two trajectories (Tc, Tc') at a constant distance from the origin (O), roughly in the form of a sinusoid comprising two periods over a complete revolution of the object and whose amplitude (Int) is equal to or greater than the distance between the origin (O) and any point of the object (11), the distance between the points of the trajectory (Tc) and the origin (O) being moreover equal to or greater than this amplitude multiplied by $\sqrt{3}$.

17. A tridimensional optical image formation method according to claim 16, wherein the second points (U) for which the quantities R'f(U) are determined have spherical coordinates ($\rho$(n), $\theta$(1), $\phi$(m)) evenly distributed and belong to the planes perpendicular to the meridian planes in which the focal spot (S) of the conical radiation occurs at the time of irradiations.

18. An optical image formation method according to claim 17, wherein the derived quantities are weighted, interpolated and added up inside each meridian plane so as to obtain quantities Q ($\rho$, B) at third points (B) belonging to a third meshing having rectangular coordinates (r(a), z(b)) evenly distributed over planes of rearranged projections of planes merged with the meridian planes and belonging to the same planes orthogonal to the meridian planes as the points (M) of the meshing representative of the object, and wherein also, for any point (B) of the third meshing, the calculations of the quantity (Q, ($\theta$,B)) characteristic of said point (B) are combined with those of the other points of the third meshing belonging to the same plane of rearranged projections.

19. A tridimensional optical image formation method according to claim 18, wherein the attenuation f(M) at any point (M) of the representative meshing is obtained by linear combination of the quantities (Q ($\rho$, B)) associated with the third points (B) of orthogonal projections of the points of the points (M) on the planes with rearranged projections.

20. A method for calculating a parameter (f(M)) on the first points (M) of a first tridimensional meshing of an object whose Cartesian coordinates are generally evenly distributed, wherein it consists firstly of defining second points (U) and third points (B) which constitute second and third tridimensional meshings of characteristic points, the spherical coordinates of the second points (U) being evenly distributed and the second points (U) belonging in particular to meridian planes converging at an axis, the third points (B), whose cylindrical coordinates are evenly distributed belong to both the meridian planes and parallel planes containing the first points (M) and orthogonal to the axis; then of obtaining information (R'f(U)) concerning the second points (U); then of deducing from this by digital processing derived information and then of combining this derived information concerning groups of second points (U) belonging to the same meridian planes so as to deduce from the intermediate information (Q ($\rho$, B)) concerning the third points (B); and finally to combine the intermediate information (Q($\rho$, B)) concerning groups of third pints (V) belonging to the same parallel planes in order to deduce from this the parameter (f(M)) concerning the first points (M).

* * * * *